(12) United States Patent
Swartz

(10) Patent No.: US 9,315,852 B2
(45) Date of Patent: Apr. 19, 2016

(54) NUCLEIC ACID-LABELED TAGS ASSOCIATED WITH ODORANT

(71) Applicant: SRC, Inc., North Syracuse, NY (US)

(72) Inventor: Mary F. Swartz, Stow, MA (US)

(73) Assignee: SRC, INC., North Syracuse, NY (US)

( * ) Notice: Subject to any disclaimer, the term of this patent is extended or adjusted under 35 U.S.C. 154(b) by 84 days.

(21) Appl. No.: 14/247,479

(22) Filed: Apr. 8, 2014

(65) Prior Publication Data

US 2014/0220583 A1    Aug. 7, 2014

Related U.S. Application Data

(62) Division of application No. 12/849,546, filed on Aug. 3, 2010, now Pat. No. 8,716,027.

(51) Int. Cl.
*G01N 37/00* (2006.01)
*C12Q 1/68* (2006.01)

(52) U.S. Cl.
CPC . *C12Q 1/68* (2013.01); *Y10T 436/13* (2015.01)

(58) Field of Classification Search
None
See application file for complete search history.

(56) References Cited

U.S. PATENT DOCUMENTS

| | | | |
|---|---|---|---|
| 3,902,851 A | 9/1975 | Dravnieks | |
| 4,104,029 A | 8/1978 | Maier, Jr. | |
| 5,090,232 A | 2/1992 | Wakabayashi et al. | |
| 5,139,812 A | 8/1992 | Lebacq | |
| 5,451,505 A | 9/1995 | Dollinger | |
| 5,635,405 A | 6/1997 | Brouwer | |
| 5,665,538 A | 9/1997 | Slater et al. | |
| 5,763,176 A | 6/1998 | Slater et al. | |
| 5,801,297 A | 9/1998 | Mifsud et al. | |
| 5,819,124 A * | 10/1998 | Somner | G08B 13/19632 396/263 |
| 5,918,257 A | 6/1999 | Mifsud et al. | |
| 5,976,886 A | 11/1999 | Cheeseman | |
| 6,025,200 A | 2/2000 | Kaish et al. | |
| 6,303,290 B1 | 10/2001 | Liu et al. | |
| 6,312,911 B1 | 11/2001 | Bancroft et al. | |

(Continued)

FOREIGN PATENT DOCUMENTS

| | | |
|---|---|---|
| CA | 2415226 | 10/2003 |
| EP | 1384790 | 1/2004 |

(Continued)

OTHER PUBLICATIONS

Murphy, G. et al. Early experience with aroma tagging and electronic nose technology for log tracking, 2004, Forest Products Journal, vol. 54(2), pp. 28-35.*

(Continued)

*Primary Examiner* — Robert Xu
(74) *Attorney, Agent, or Firm* — George McGuire; Blaine Bettinger; Bond Schoeneck & King, PLLC

(57) ABSTRACT

A nucleic acid tag comprising a nucleotide-support platform attached to a nucleic acid molecule, an odorant, and an encapsulant. Unique nucleic acid-containing tags containing an odorant are seeded at one or more geographic locations. Using odorant-detection systems, the person or object of interest is examined for the presence of one or more of the odorant, thereby revealing the presence of the seeded nucleic acids and eliminating the expense and time associated with unnecessary screening. The geographic location associated with each detected nucleic acid is used to backtrack the item's path or extrapolate a probable point of origin.

8 Claims, 15 Drawing Sheets

(56) References Cited

U.S. PATENT DOCUMENTS

| | | |
|---|---|---|
| 6,423,551 B1 | 7/2002 | Weiss et al. |
| 6,477,227 B1 | 11/2002 | Kaiser et al. |
| 6,537,747 B1 | 3/2003 | Mills, Jr. et al. |
| 6,548,264 B1 | 4/2003 | Tan et al. |
| 6,647,649 B2 | 11/2003 | Hunt et al. |
| 6,677,043 B2 | 1/2004 | Kunitake et al. |
| 6,680,211 B2 | 1/2004 | Barbera-Guillem et al. |
| 6,686,167 B2 | 2/2004 | Bagaria |
| 6,689,338 B2 | 2/2004 | Kotov |
| 6,692,967 B1 | 2/2004 | Di Benedetto et al. |
| 6,721,083 B2 | 4/2004 | Jacobson et al. |
| 6,727,065 B2 | 4/2004 | Weiss et al. |
| 6,764,856 B2 | 7/2004 | Holmes et al. |
| 7,033,754 B2 | 4/2006 | Chee et al. |
| 7,067,264 B2 | 6/2006 | Bagaria |
| 7,071,913 B2 | 7/2006 | Albert et al. |
| 7,115,301 B2 | 10/2006 | Sheu et al. |
| 7,237,504 B2 | 7/2007 | Davis et al. |
| 7,333,268 B2 | 2/2008 | Steenblik et al. |
| 7,357,043 B2 | 4/2008 | Cumming et al. |
| 7,359,802 B1 | 4/2008 | Lewis et al. |
| 7,477,993 B2 | 1/2009 | Sunshine et al. |
| 7,531,136 B2 | 5/2009 | Besnard et al. |
| 7,607,338 B1 | 10/2009 | Lewis et al. |
| 7,645,884 B2 | 1/2010 | Chauhan et al. |
| 7,687,244 B1 | 3/2010 | Fischer |
| 7,767,457 B2 | 8/2010 | Mun et al. |
| 2004/0105979 A1 | 6/2004 | Bayless |
| 2004/0166520 A1 | 8/2004 | Connolly |
| 2005/0026181 A1 | 2/2005 | Davis et al. |
| 2005/0053968 A1 | 3/2005 | Bharadwaj et al. |
| 2005/0147974 A1 | 7/2005 | Muller-Shulte |
| 2005/0158390 A1 | 7/2005 | Rana et al. |
| 2005/0191665 A1 | 9/2005 | Su et al. |
| 2006/0083694 A1 | 4/2006 | Kodas et al. |
| 2006/0088946 A1 | 4/2006 | Willson et al. |
| 2006/0260941 A1 | 11/2006 | Tan et al. |
| 2007/0042372 A1 | 2/2007 | Arita |
| 2007/0087385 A1 | 4/2007 | Muller-Schulte |
| 2007/0106006 A1 | 5/2007 | Cooper et al. |
| 2007/0172653 A1 | 7/2007 | Berkland et al. |
| 2007/0190100 A1 | 8/2007 | Shastri et al. |
| 2007/0298006 A1 | 12/2007 | Tomalia et al. |
| 2008/0035021 A1 | 2/2008 | Sambasivan et al. |
| 2008/0037131 A1 | 2/2008 | Steenblik et al. |
| 2008/0075667 A1 | 3/2008 | Berkland et al. |
| 2008/0166557 A1 | 7/2008 | Bayless |
| 2008/0241262 A1 | 10/2008 | Lee et al. |
| 2009/0004670 A1 | 1/2009 | Zhang et al. |
| 2009/0065583 A1 | 3/2009 | McGrew |
| 2009/0075261 A1 | 3/2009 | Hayward et al. |
| 2009/0229983 A1 | 9/2009 | Tan et al. |

FOREIGN PATENT DOCUMENTS

| | | |
|---|---|---|
| KR | 20080060060 | 7/2008 |
| WO | 2008074340 | 6/2008 |
| WO | 2008090664 | 7/2008 |

OTHER PUBLICATIONS

Zelikin et al.; A General Approach for DNA Encapsulation in degradable Polymer Microcapsules; ACS Nano, vol. 1, No. 1, pp. 63-69 (2007).

Heider et al.; DNA-based watermarks using the DNA-Crypt algorithm; BMC Bioinformatics 2007; http://www.biomedcentral.com/1471-2105/8/176.

Gehani et al.; DNA-Based Cryptography; Aspects of Molecular Computing, pp. 34-50; Springer, Berlin, Heidelberg (2004).

Labean et al.; Experimental Progress in Computation by Self-Assembly of DNA Tilings; DIMACS Series in Discrete Mathematics and Theoretical Computer Science, vol. 54, pp. 123-140, MIT, Cambridge, 2000.

Rauhe et al.; Digital DNA Molecules; Proceedings 6th DIMACS Workshop on DNA Based Computers, held at the University of Leiden, The Netherlands, Jun. 13-17, 2000.

Kang; A Pseudo DNA Cryptography Method; www.comp.nus.edu.sg, 2009.

Roy et al.; Optical tracking of organically modified silica nanoparticles as DNA carriers: A nonviral, nanomedicine approach for gene delivery; PNAS, vol. 102, No. 2, pp. 279-284 (2005).

Quickenden et al.; Luminescence, 2001, 16:251-253.

Bohannon, John, "Smart Coatings' Research Shows The Virtues of Superficiality" 309 (5733) Science, pp. 376-377 (2005).

* cited by examiner

NUCLEIC ACID-LABELED TAGS ASSOCIATED WITH ODORANT

CROSS-REFERENCE TO RELATED APPLICATIONS

This application is a divisional of U.S. patent application Ser. No. 12/849,546, filed on Aug. 3, 2010, the entirety of which is hereby incorporated by reference.

BACKGROUND OF THE INVENTION

1. Field of the Invention

The present invention relates to nucleic acid-labeled tags, and, more particularly, to the use of an odorant as a screening element for the detection of odorant-labeled nucleic acid-labeled tags.

2. Description of the Related Art

The physical characteristics of a nucleic acid molecule make it uniquely suitable for use as a secure information-storage unit. In addition to being odorless and invisible to the naked eye, a nucleic acid molecule can store vast amounts of information. It has been estimated that a single gram of deoxyribonucleic acid ("DNA") can store as much information as approximately one trillion compact discs ("Computing With DNA" by L. M. Adleman, *Scientific American*, August 1998, pg 34-41).

Nucleic acid molecules are also resilient to decay, even in vitro. Although a nucleic acid molecule typically begins to breakdown when exposed to chemicals, radiation, or enzymes, some nucleic acid molecules can survive for thousands of years. For example, scientists have sequenced the Neanderthal genome using DNA molecules that were recovered from remains dating at least 38,000 years old.

Lastly, nucleic acid molecules are both ubiquitous in nature and largely uncharacterized, with only a fraction of the world's organisms having been sequenced. As a result of this uncharacterized environmental background noise, inadvertent detection of a man-made nucleic acid molecule is unlikely.

To employ the many beneficial characteristics of nucleic acids, these molecules can be incorporated into a secure tag. These tags can be composed of deoxyribonucleotides, ribonucleotides, or similar molecules composed of nucleic acids that are either artificial (such as nucleotide analogues) or are otherwise found in nature. The nucleic acids can range from very short oligonucleotides to complete genomes.

Once a nucleic acid tag is created it can be used for numerous unique security applications including to: (i) detect illicit tampering with physical objects; (ii) secure the privacy of a room or building; (iii) send encoded messages between individuals; (iv) detect a tagged individual or object at a distance; (v) track the recent travel history of an individual or object; or (vi) monitor a location of interest.

DNA tags have previously been used for other applications. For example, DNA tags have been removably attached to tangible assets to assist in the identification of ownership in the event the asset is lost or stolen. Additionally, it has been proposed that DNA tags be used to prevent counterfeiting by incorporating tags into items during or after production and using detection of such tags to authenticate the items.

SUMMARY OF THE INVENTION

It is therefore a principal object and advantage of the present invention to provide a nucleic acid tag that can be used in numerous security-related applications.

It is a further object and advantage of the present invention to provide a method of standoff detection using nucleic acid tags.

It is yet another object and advantage of the present invention to provide a method of determining whether an object has traveled through a location using seeded nucleic acid-labeled tags.

It is a further object and advantage of the present invention to backtrack or identify an object's point of origin or recent geographic course using seeded nucleic acid-labeled tags.

It is yet another object and advantage of the present invention to provide an odorant-associated nucleic acid-labeled tag.

It is a further object and advantage of the present invention to provide a nucleic acid-labeled tag that with an odorant that co-locates with the tag.

It another object and advantage of the present invention to provide a nucleic acid-labeled tag that with an odorant that, with its presence or absence, indicates the presence or absence of the tag.

It is yet another object and advantage of the present invention to provide a nucleic acid-labeled tag that with an odorant that cannot be discerned by a human without the aid of an odorant detection device.

It is a further object and advantage of the present invention to provide a nucleic acid-labeled tag that with an odorant that is covert, non-toxic, and which does not inhibit PCR analysis.

It is another object and advantage of the present invention to provide a nucleic acid-labeled tag that with an odorant that cannot be detected with odor detection equipment unless the equipment has been trained to identify the odorant in an operational setting.

Other objects and advantages of the present invention will in part be obvious, and in part appear hereinafter.

In accordance with the foregoing objects and advantages, the present invention provides a nucleic acid tag, the tag comprising: a nucleotide-support platform attached to a nucleic acid molecule; and an odorant. According to one embodiment, the odorant is a synthetic chemical, although it can be any chemical known to be capable of detection with or without the aid of an odorant detection device.

Another embodiment of the present invention provides for a nucleic acid tag, the tag comprising: a nucleotide-support platform attached to a nucleic acid molecule; an odorant; and an encapsulant, where the encapsulant is adapted to prevent degradation of the nucleic acid molecule.

A further embodiment of the present invention provides a method of determine whether an item has moved through a geographic location, the method comprising: seeding a geographic location with a nucleic acid tag comprised of a nucleotide-support platform attached to a nucleic acid molecule, and further comprising an odorant; and screening the item for the presence or absence of the nucleic acid tag.

Another embodiment of the present invention provides a method of determine whether an item has moved through a geographic location, the method comprising: seeding a geographic location with a nucleic acid tag comprised of a nucleotide-support platform attached to a nucleic acid molecule, and further comprising an odorant; and screening the item for the presence or absence of the nucleic acid tag, where the step of screening comprises the steps of screening the item for the presence of the odorant, and if the odorant is present, characterizing the nucleic acid tag.

Yet another embodiment of the present invention is a method for backtracking the travel history of an item, the method comprising: seeding a first geographic location with a first nucleic acid, the first nucleic acid tag comprising a first nucleotide-support platform attached to at least a first nucleic acid molecule and further comprising an odorant; seeding a second geographic location with a second nucleic acid, where the second nucleic acid tag comprises a second nucleotide-support platform attached to at least a second nucleic acid molecule and further comprising an odorant; screening the item for the presence or absence of one or more nucleic acid tags; and identifying the geographic location associated with each nucleic acid tag detected on the item.

A further embodiment of the present invention is a method for backtracking the travel history of an item, the method comprising: seeding a first geographic location with a first nucleic acid, the first nucleic acid tag comprising a first nucleotide-support platform attached to at least a first nucleic acid molecule and further comprising an odorant; seeding a second geographic location with a second nucleic acid, where the second nucleic acid tag comprises a second nucleotide-support platform attached to at least a second nucleic acid molecule and further comprising an odorant; screening the item for the presence or absence of one or more nucleic acid tags, where the step of screening further comprises the steps of screening the item for the presence of the odorant, and if the odorant is present, characterizing the one or more nucleic acid tags; and identifying the geographic location associated with each nucleic acid tag detected on the item.

Another embodiment of the present invention is a method for determining the point of origin of an item, the method comprising: seeding each of two or more geographic locations with a unique nucleic acid tag, the tag comprising a nucleotide-support platform attached to at least one nucleic acid molecule, and further comprising an odorant; screening the item for the presence or absence of one or more nucleic acid tags; identifying the geographic location associated with each nucleic acid tag detected on the item; and extrapolating the point of origin.

Yet another embodiment of the present invention is a method for determining the point of origin of an item, the method comprising: seeding each of two or more geographic locations with a unique nucleic acid tag, the tag comprising a nucleotide-support platform attached to at least one nucleic acid molecule, and further comprising an odorant; screening the item for the presence or absence of one or more nucleic acid tags, where the step of screening further comprises the steps of screening the item for the presence of the odorant, and if the odorant is present, characterizing the one or more nucleic acid tags; identifying the geographic location associated with each nucleic acid tag detected on the item; and extrapolating the point of origin.

BRIEF DESCRIPTION OF THE DRAWINGS

The present invention will be more fully understood and appreciated by reading the following Detailed Description of the Invention in conjunction with the accompanying drawings, in which.

DETAILED DESCRIPTION OF THE INVENTION

Figure 1:
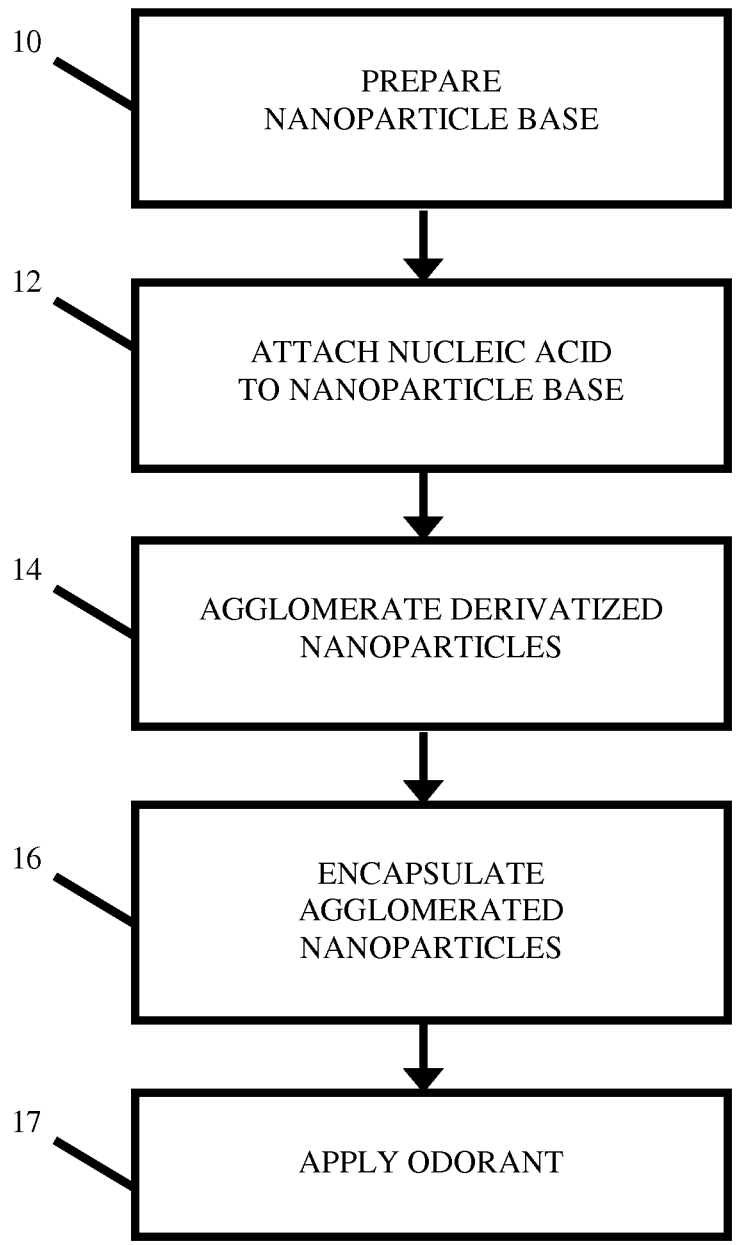
FIG. 1 is a schematic representation of nucleic acid tag production.

Referring now to the drawings wherein like reference numerals designate identical or corresponding parts throughout the several views, there is shown in FIG. 1 a schematic representation of nucleic acid tag production. As an initial step 10, a nanometer-sized particle ("nanoparticle") platform is prepared for attachment to the nucleic acid molecule(s). A platform is used to make the nucleic acid more accessible to downstream analysis and prevent nucleic acid loss if any portion of the encapsulating layer is compromised.

The platform is any compound that can be attached to nucleic acid without unintentionally degrading or altering the nucleic acid sequence. For example, the platform can be a lightweight, durable, non-water soluble, and chemically inert structure composed of silica or polystyrene. Additionally, the nanoparticle platform should be composed of a compound that does not inhibit any downstream analysis of the nucleic acid molecules, including tag detection and polymerase chain reaction (PCR).

In step 12, the nucleic acid molecule is attached to the prepared nanoparticle platform. The nucleic acid molecules are optimally attached to the nanoparticle to facilitate later analysis. In a preferred embodiment, a chemical linker is used to connect the nucleic acid to the nanoparticle platform. This chemical linker must keep the nucleic acid securely tethered to the nanoparticle while avoiding inhibition of the detection or analysis of the tag and nucleic acid. Although the chemical linker can be chosen to provide a permanent covalent link between the nucleic acid and the nanoparticle platform, it could also be a compound that quickly and efficiently releases the nucleic acid at a certain temperature or after exposure to a release compound. In one embodiment, the chemical linker is the odorant, or also links to the odorant. This embodiment guarantees co-localization of the odorant and the nucleic acid-labeled tag, potentially provides stability to the odorant, and potentially provides for efficient downstream analysis of the associated nucleic acid.

The nucleic acid molecule can also be designed to promote analysis. For example, to avoid steric hindrance or unwanted intermolecular interactions, the molecule can include nucleotide spacers between the chemical linker or nanoparticle base and the information-coding segment of the nucleotide sequence. Spacing between 5 and 15 bases has been optimal for current applications, although this may vary as new applications are considered.

The concentration of nucleic acid molecules on the nanoparticle platform is also an important factor in downstream analysis. If the molecules are too concentrated, steric hindrance prevents the primer and polymerase from efficiently binding the proper segments of the nucleic acid molecules. If the molecules are too sparse, the PCR signal will be diminished and can result in false negatives. In the preferred embodiment, a concentration of about $3\times10^{10}$ nucleic acid molecules per square centimeter is the optimal concentration for robust PCR signal.

In step 14, the nucleic acid-derivatized nanoparticles are agglomerated. Agglomeration protects the nucleic acid molecules from degradation and facilitates encapsulation. To agglomerate the particles to the desired size range, the nanoparticles are vacuum dried, milled, and sieved.

Compounds might be used or incorporated into the tag to promote disagglomeration of the agglomerates prior to PCR analysis. These compounds might be bovine serum albumin, salmon sperm DNA, carbohydrates, polyvinyl alcohol, fructose, or chitosan, among others. With more nucleic acid exposed during dissolution, subsequent analysis will be faster and more sensitive.

After the nanoparticles are agglomerated, the agglomerates can be encapsulated in step 16. The encapsulant protects the nucleic acid from degradation by ultraviolet light, hydrolysis, enzymatic digestions, chemical degradation, or any other means. Additionally, the encapsulant can be designed such that it does not hinder analysis of the nucleic acid molecules. For example, the encapsulant should not contain any compounds that would inhibit or prevent a PCR reaction, although efficient removal of the encapsulant before PCR analysis would eliminate this requirement. Additionally, the encapsulant should enhance the ability of the tag to discretely attach to people and objects. If covertness is required, the encapsulant can be designed to deter detection.

The encapsulating layer can also be designed with surface moieties added to the inner or outer surfaces of the encapsulant or incorporated into the encapsulant material. The moieties are designed to facilitate a particular use of the nucleic acid tag. For example, the moiety can be hydrophobic to enable stickiness or contain antibodies designed for specific targeting. The molecular interactions between the moiety and a target compound can range from simple electrostatic interactions to antibody-antigen recognition. The moiety can also promote detection of the nucleic acid tag. In one embodiment, the encapsulating layer is composed of or comprises an odorant that promotes detection of the tag, as discussed in detail below.

To protect the nucleic acid from degradation, the encapsulating layer can be coated with or include another functional layer of material. For example, the encapsulant can be coated with or include a non-water-soluble compound to prevent access to water or similar molecules. The encapsulant can also be coated with or include a UV-blocking compound such as titanium dioxide to prevent UV-induced degradation of the nucleic acid molecules.

The tag can also include an odorant, as shown in step 17 of FIG. 1. The odorant is preferably anything known to be capable of detection by mechanical means or by human or animal means (i.e., olfaction detection). The odorant can comprise anything known by those skilled in the art to be capable of detection, including a single aromatic, a blend of aromatics, or a commercially available synthetic chemical, among many others. Since the surfaces on which the odorant might be detected will vary, the odorant will preferably be unique or distinctive enough to be detected over random odorants present on these surfaces or in the surrounding environment. Although according to one embodiment the odorant is capable of detection by humans and/or animals, in the preferred embodiment the odorant can only be detected by animals and/or electronic means, thereby evading human detection. For example, mechanical means such as an "electronic nose" could be programmed or trained to recognize the odorant and alert the user to its presence. In a preferred embodiment, the sensor provides quantitative information about detection and is sensitive enough to detect very minute or trace amounts of the odorant.

Figure 2:
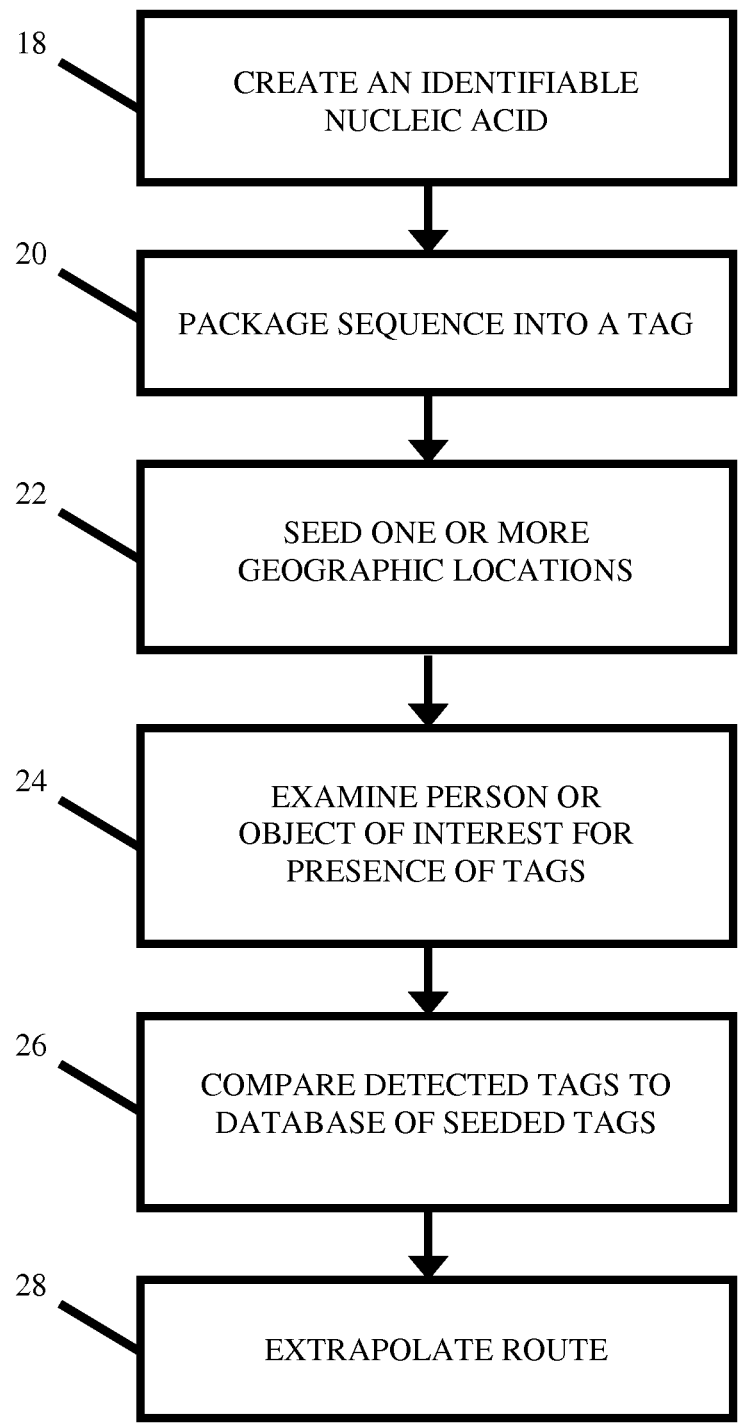
FIG. 2 is a schematic representation of an embodiment of the method according to the present invention.

FIG. 2 is a schematic representation of an embodiment of a security method according to the present invention. More specifically, the figure represents characterization of the recent travel history of point of an item. An item can be any person or object of interest. Seeding an area with tags that naturally or artificially adhere to objects (including people or animals) provides a mechanism for identifying the origin of those objects simply by analyzing the adhering tags. Similarly, by seeding different areas with discernibly different tags it is possible to backtrack the geographic path that an object has followed. Such a mechanism would allow the seeder—the person or organization who seeded and will analyze the tags—to identify the recent travel history of the person or object; to quickly identify people or objects that have traveled through seeded areas; and to identify vehicles that have traveled through seeded areas and might carry dangerous cargo such as explosives, among other uses.

As an initial step 18, an identifiable nucleic acid is characterized or created. In one embodiment of the present invention, the sequence ranges from a short oligonucleotide to an entire genome and is generated through any of the various known methods of natural or artificial nucleic acid synthesis. The nucleic acid can be completely composed of either natural nucleic acids which normally compose the genomes of organisms, artificial nucleic acids, or a mixture of the two.

In the preferred embodiment of the tag, the nucleic acid molecules of each type of tag—which typically differ depending on location or manner of use—contain identical primer-binding sequences surrounding unique nucleotide sequences. Each unique nucleotide sequence contained between the primers encodes information that corresponds to the location, time, or other data specific to that unique sequence. Since analysis of a detected tag uses the same primers, the analysis is performed faster and more efficiently.

The primer sequences, whether they are unique or identical for each location or use, are chosen to avoid cross-reactions with naturally-occurring nucleic acid molecules in the environment in which the tag is located. Although only a fraction of natural nucleic acid molecules on Earth have been characterized by scientists, the search of nucleic acid repository databases such as GenBank®, the National Institutes of Health database containing all publicly available DNA sequences, should be a preliminary step in constructing the primer sequences.

In one embodiment of the current invention, unique groupings of nucleotides are assigned a specific letter, number, or symbol value in order to encode information within the sequence. By placing the unique groupings in order, information can be encrypted into the nucleotide sequence. To further increase the security of the information, advanced encryption algorithms can be used to assign letter, number, or symbol values to specific nucleotides or nucleotide groupings. Additionally, the encryption system can be periodically changed to prevent decryption by intercepting entities.

The nucleic acid can also be encoded to contain information other than a string of letters, numbers, and symbols. For instance, the sequence can be a random sequence that corresponds to the latitude and longitude of the site that will be seeded. Alternatively, the tag can be as simple as a single nucleic acid change in a previously identified or known sequence. For example, the nucleotide sequence can be embedded in a full or partial genomic sequence corresponding to an organism which naturally exists in the location to be seeded. Modifications to the natural nucleic acid sequence, known only to the creator of the tag, can be made such that the changes resemble natural variations of the sequence and thus fail to arouse suspicion, even by individuals that might suspect such tags are present.

To decrypt the encoded information according to this system, an individual will need: (1) knowledge that encoded nucleic acid is present; (2) knowledge of the specific location of the information within the nucleic acid in order to use the appropriate primers for amplification and sequencing reactions; (3) access to a PCR machine and reagents; and (4) the encryption algorithm, or, alternatively, complex decryption capabilities.

Although creating the tag within the genome of an naturally-occurring organism provides numerous benefits, both in vivo and in vitro DNA replication occasionally introduces random errors into a DNA sequence despite the actions of proof-reading and repair enzymes. By deleting one or more nucleotides or frame-shifting the nucleic acid sequence, these mutations can disrupt any encrypted information contained therein. Computer algorithms are used to restore the information by recognizing and repairing the errors. For example, if a mutation adds one or more nucleotides to a pre-defined sequence and disrupts the information, the algorithm removes single or multiple nucleotides from the sequence until the information is corrected. Similarly, if a mutation removes one or more nucleotides, the algorithm systematically adds nucleotides to the sequence until the information is corrected. The algorithm must also be robust enough to decrypt sequences that contain more than one type of error-inducing mutation, and must be capable of recognizing when the information contained with the nucleic acid has been restored.

Figure 3:
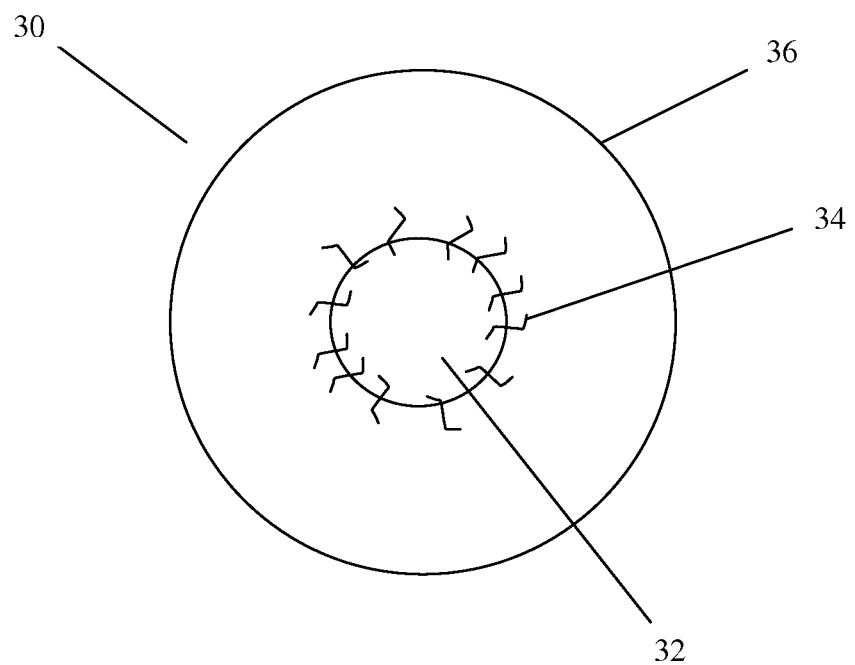
FIG. 3 is a side view of an encapsulated nucleotide tag complex.

In step 20 of FIG. 1, the nucleic acid is packaged into an appropriate tag complex. To avoid potentially harmful environmental side-effects, the tag can be large enough to avoid being inhaled by people or organisms but small enough to be covert. FIG. 3 represents one embodiment of this tag structure. Tag 30 is composed of a single nucleotide-support platform 32, nucleic acid 34, and encapsulant 36.

Figure 4:
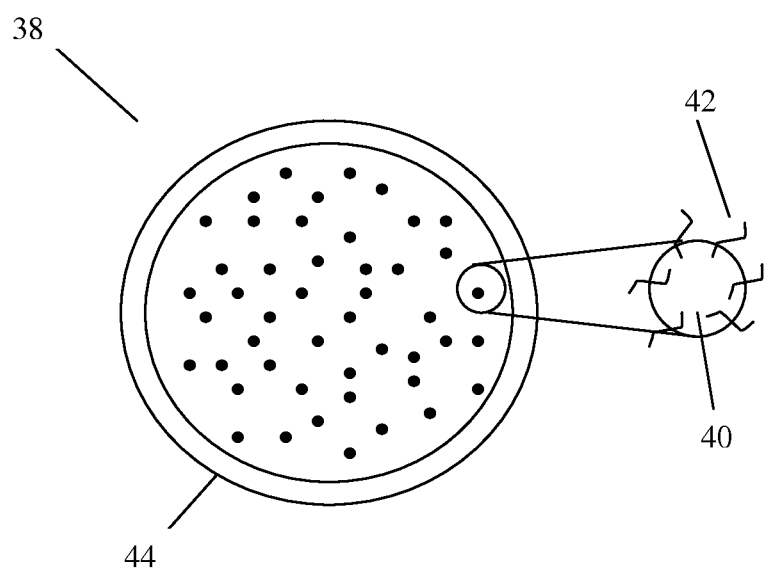
FIG. 4 is a side view of encapsulated nucleotide-derivatized nanoparticles.

FIG. 4 is a side view of another embodiment of the tag structure. Tag 38 is composed of nucleotide-support platform 40 derivatized with nucleic acid 42 and surrounded by encapsulant 44. Similar to the tag in FIG. 3, tag 38 contains nucleic acids that are contained within an encapsulant that protects the sequence without inhibiting later analysis. Unlike the bead platform used by the tag in FIG. 3, nucleotide-support platform 40 is composed of nanoparticles. Tag 38 can contain thousands, millions, or even billions of nucleotide-derivatized nanoparticles within the encapsulant layer. In several of the described embodiments, the encapsulant layer must be designed to prevent inhibition of excitation and emission wavelengths.

Figure 5:
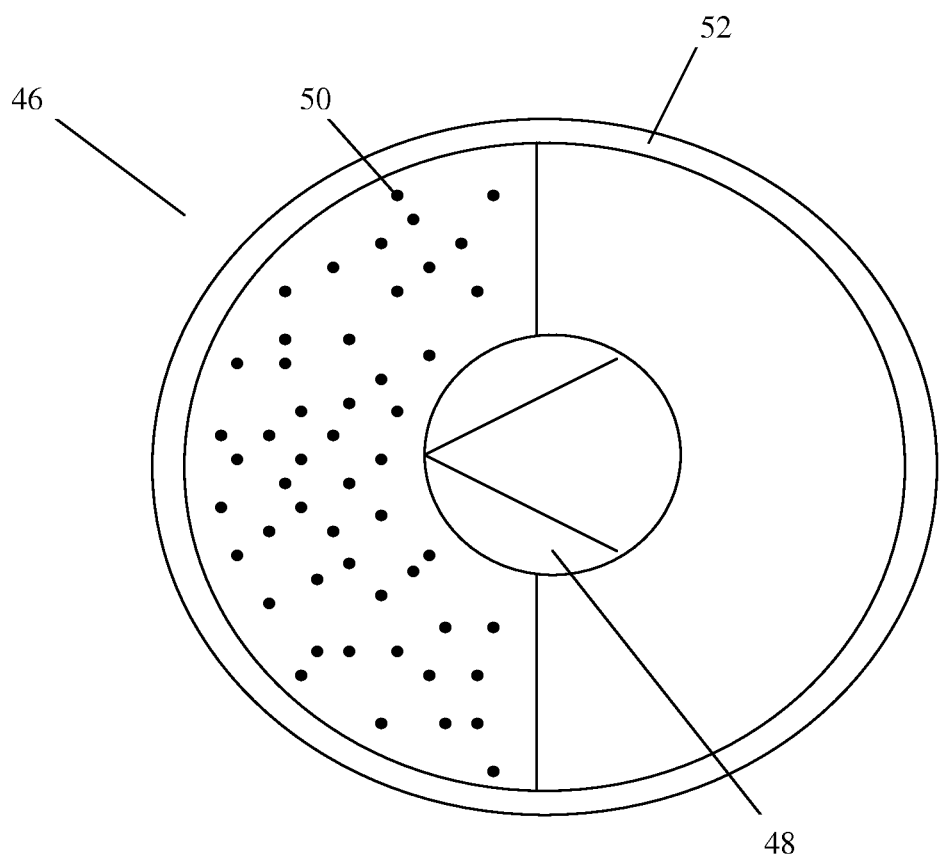
FIG. 5 is a side view of an encapsulated tag complex containing a retroreflector and nucleotide-derivatized nanoparticles.

FIG. 5 is yet another embodiment of the tag complex. Encapsulated tag 46 contains a retroreflector 48, nucleotide-derivatized nanoparticles 50, and encapsulant 52. Retroreflector 48, a device that reflects an electromagnetic wave front back along a vector that is parallel to but opposite in direction from the angle of incidence, forms the center of tag 46. The retroreflector must be situated to allow electromagnetic waves to hit and reflect from the surface. To prevent obstruction of the retroreflector, the tag is organized to keep nucleotide-derivatized nanoparticles 50 away from the surface of the retroreflector, as shown in FIG. 5. Additionally, encapsulant 52 must protect the tag complex without interfering with the retroreflector's reflectivity. As an alternative to the nanoparticle format shown in FIG. 5, the nucleic acid can coat the non-reflective surfaces of retroreflector 48. In another embodiment of the retroreflector tag, the non-reflective surfaces of the retroreflector are coated with nucleic acid and only those surfaces are covered by a protective encapsulant.

In yet another embodiment, the tag complex can include an odorant 56 that provides a preliminary level of screening. By quickly and affordably pre-screening for the presence of the odorant, the screener can determine whether the tag might be present without performing swabs or extensive downstream DNA analysis, thereby lowering the time and cost associated with screening.

Figure 6:
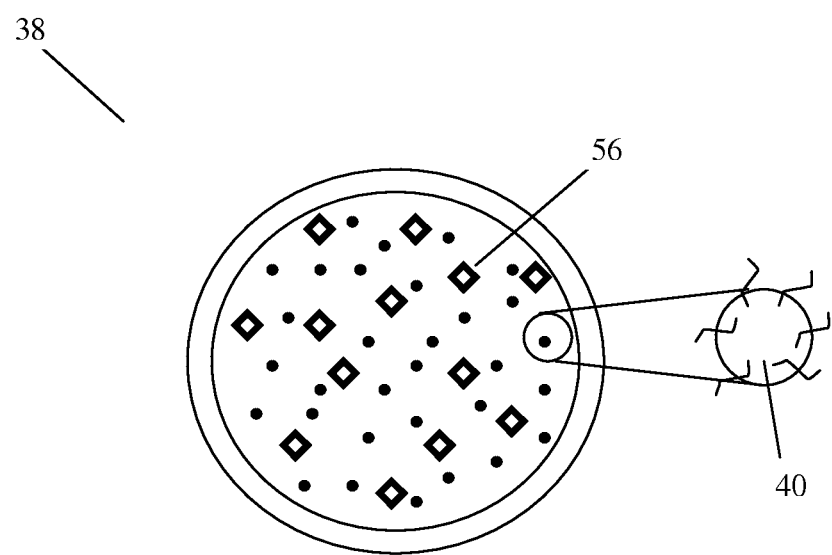
FIG. 6 is a side view of an encapsulated nucleotide tag complex with odorant trapped inside the tag by the encapsulant layer.
Figure 7:
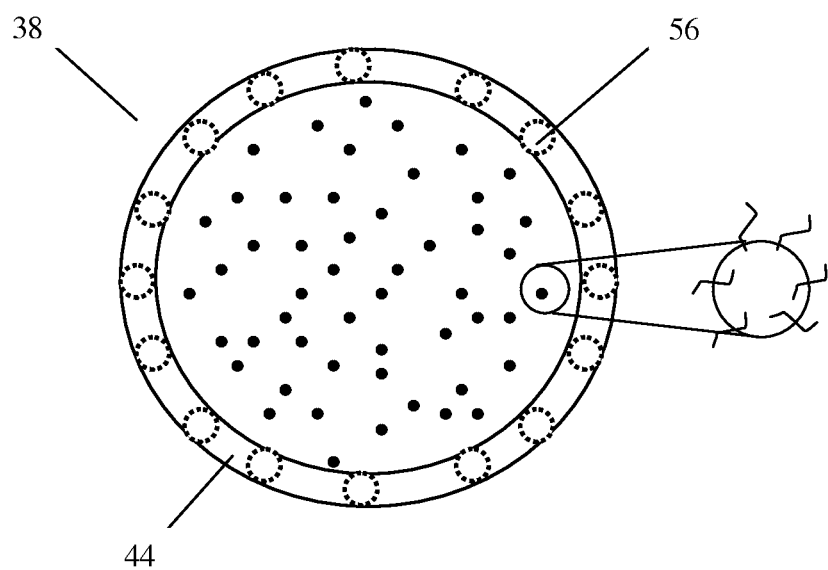
FIG. 7 is a side view of an encapsulated nucleotide tag complex with odorant incorporated into the encapsulant layer.
Figure 8:
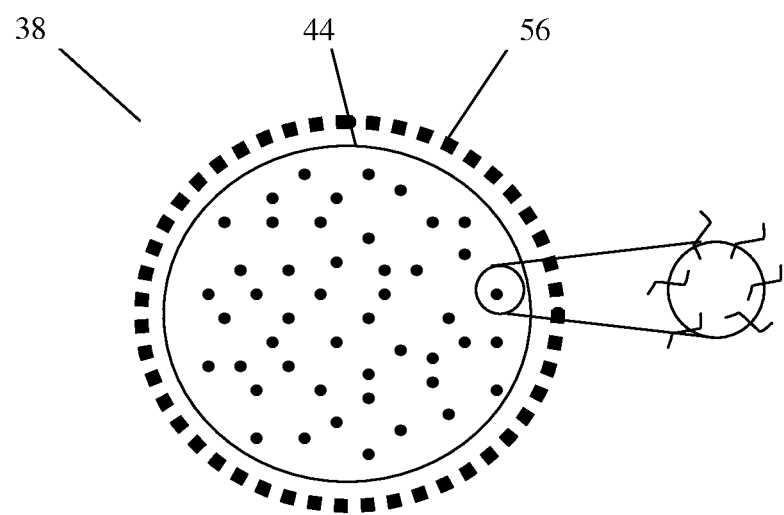
FIG. 8 is a side view of an encapsulated nucleotide tag complex with odorant coating the outer surface of the encapsulant.
Figure 9:
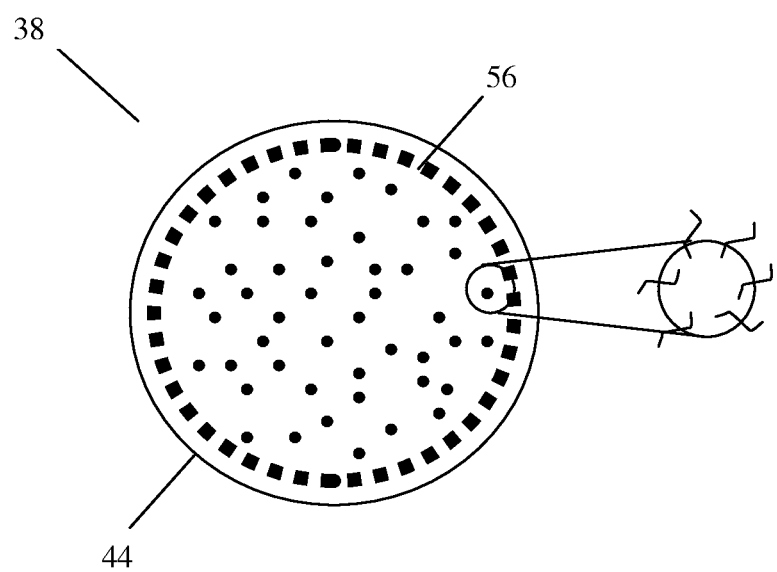
FIG. 9 is a side view of an encapsulated nucleotide tag complex with odorant coating the inner surface of the encapsulant.
Figure 10:
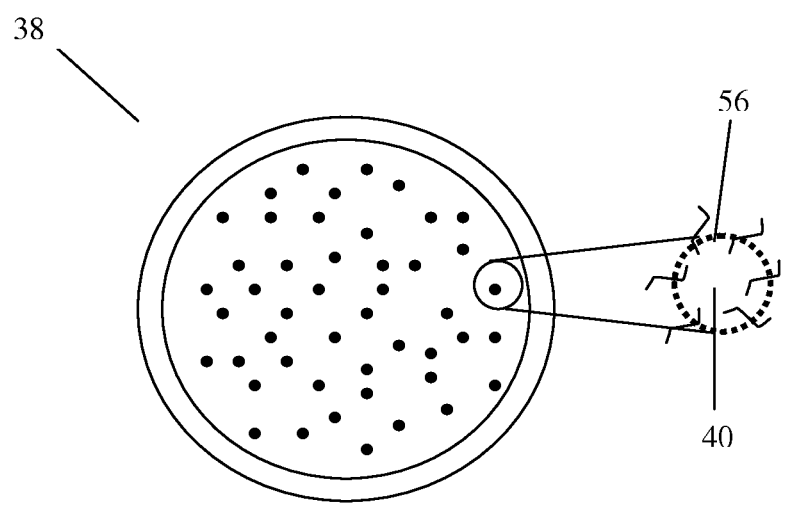
FIG. 10 is a side view of an encapsulated nucleotide tag complex with odorant incorporated into the nanoparticles.

The odorant 56 can be incorporated into the tag in a number of different ways. For example, in FIG. 6 the odorant is separate from nucleotide-support platform 40 and encapsulant 44 but is trapped within the interior of tag 38. In this configuration, the encapsulant must be constructed such that the odorant is capable of detection. In FIG. 7, odorant 56 is incorporated into encapsulant 44. In FIG. 8, the odorant forms a layer on the exterior surface of the encapsulant. Odorant 56 could also coat the interior surface of the encapsulant, as shown in FIG. 9. In FIG. 10, the odorant coats the surface of nucleotide-support platform 40.

In step 22 of FIG. 2, one or more geographic locations are seeded with the tags. The locations are seeded with tags using any mechanism that will adequately disperse the tags at the desired concentration. For example, the tags can be seeded on and along roadways or paths using an automobile that has been modified to disperse the tags. The tags can also be discretely dispersed from the air using an airplane or remotely-controlled flying apparatus. Tags can even be seeded by individuals using hand-held dispersal systems.

To efficiently backtrack the movements of a person, vehicle, or object, each road within a given location can be seeded with a unique tag. As the vehicle moves through the location it picks up tags from each road it traverses. This system can be scaled up or scaled down to suit the needs of the seeder. For example, rather than seeding individual roads the seeder can use the tags to label large regions of land to backtrack large-scale movements. Alternatively, the seeder can scale down the method by seeding individual homes or buildings to identify individuals or objects that have entered those buildings.

In step 24 of FIG. 2, an item is examined for the presence of seeded tags. Once an object of interest is identified, the object can be examined for seeded tags using any mechanism designed to pick up tags from the surfaces of the object. For example, the tires, wheel wells, or underside of a vehicle can be swabbed for tags. If the object of interest is a person, the individual's clothes, shoes, hair, or skin can be swabbed for tags. If the object of interest is a post-blast fragment of an explosive device, the surfaces of the fragment can be swabbed for any tags that survived the explosion.

If the seeded tags contain an odorant, odorant-detection means such as human or animal olfaction detection or electronic sensor detection—including a chemical sensor, an electronic nose, MEMS sensor, or any other type of odorant-detection or chemical-detection sensor known to those skilled in the art—can be used to detect the presence of tags. Detection of the seeded tag by olfaction or an odorant sensor provides a number of useful advantages. For example, this screening step reduces the number of samples that must be analyzed by downstream DNA techniques. Without screening, samples must be blindly recovered from every surface and analyzed for detection of the nucleic acids. With the odorant, samples are only recovered from surfaces that likely encountered the odorant and thus the nucleic acid-labeled tag. Further, pre-screening for the odorant limits the area needed for sampling by concentrating the samples to only the areas where the odorant is detected. Alternatively, the odorant can limit the amount of work necessary to screen samples that have already been gathered. For example, if 1,000 different samples are taken from one or more surfaces, only those samples that are shown to contain odorant will be analyzed further.

In another embodiment multiple odorants could be seeded with the tags, and pre-screening would rule out the need to PCR-analyze samples for suites of tags. This embodiment would require odorants which would not interfere with the detection of other odorants, such that individual odorants could be resolved from a mixture of odorants. Multiple sensors could be employed in this embodiment.

If the seeded tags contain retroreflectors, electromagnetic waves can be used to detect the presence of tags. Scanning equipment shines light on the object of interest and looks for a wave front that is reflected along a vector that is parallel to but opposite in direction from the wave's source. This suggests that retroreflective tags are present on the surface of the object and alerts the authorities that further investigation is necessary. This rapid and cost-effective identification of retroreflective tags is especially useful for high-throughput locations such as checkpoints and border crossings. Once the retroreflective tags are detected, they can be removed from the surfaces of the object for analysis of the attached nucleic acids to identify geographic locations.

The tags can also contain luminescent compounds that reveal their presence from a distance. Although the preferred embodiment uses fluorescent or phosphorescent photoluminescence, other embodiments may include chemiluminesent, radioluminescent, or thermoluminescent compounds. The photoluminescent compound is chosen such that absorption of a photon with a certain wavelength by the compound causes the emission of a photon with a different wavelength. The difference between the wavelength of the absorbed photon and the wavelength of the emitted photon depends on the inherent physical properties of the chosen compound.

In the preferred embodiment, the luminescent compound absorbs and emits photons in the ultraviolet band—between 10 and 400 nanometers—of the electromagnetic spectrum. The compound is chosen to avoid interference by UV radiation from the sun. The Earth's atmosphere absorbs as much as 99% of the UV radiation emitted by the sun in the 150-320 nm range. Thus the most advantageous luminescent compound absorbs and emits photons with wavelengths below 320 nm.

As an alternative to luminescent compounds that absorb and emit photons in the 150-320 nm range, compounds that absorb and emit photons of wavelengths greater than 320 nm can be used under certain circumstances. For example, these compounds could be used during nighttime conditions or in an enclosed UV-blocking environment such as a windowless structure.

Figure 11:
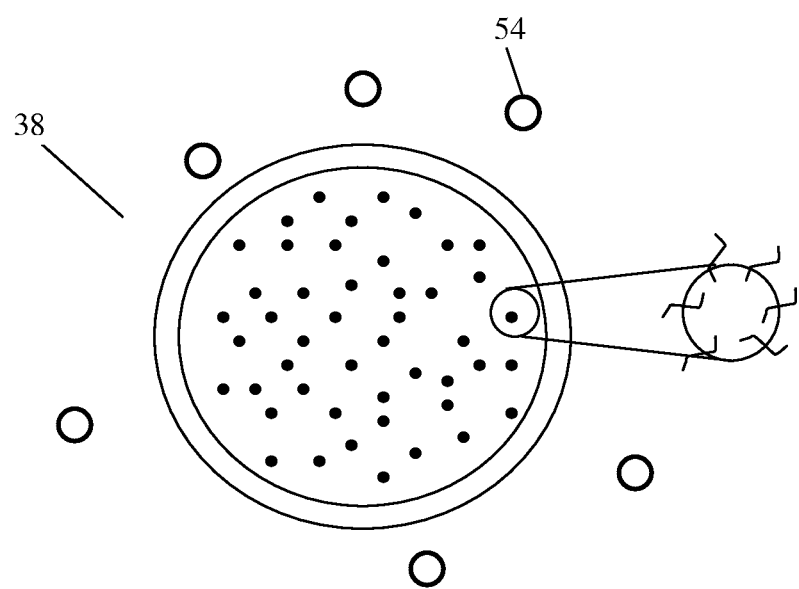
FIG. 11 is a side view of an encapsulated nucleotide tag complex with separate marker elements.
Figure 12:
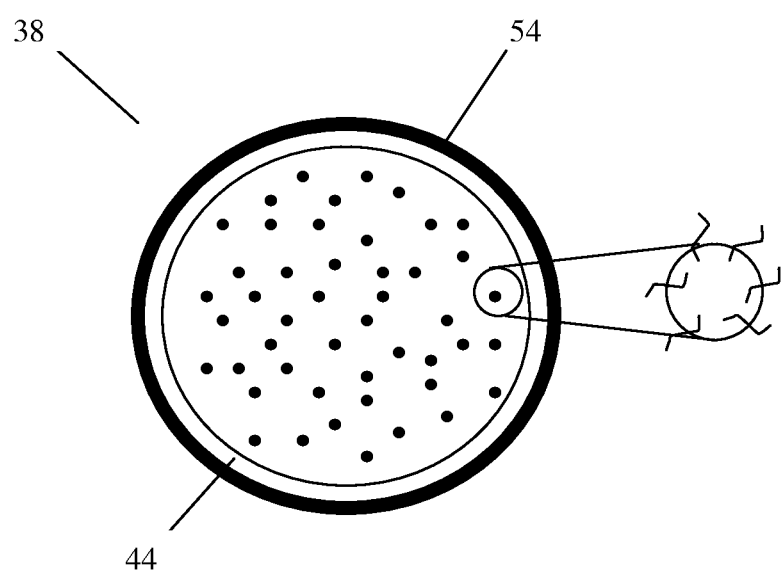
FIG. 12 is a side view of an encapsulated nucleotide tag complex with marker elements coating the outer surface of the encapsulant.
Figure 13:
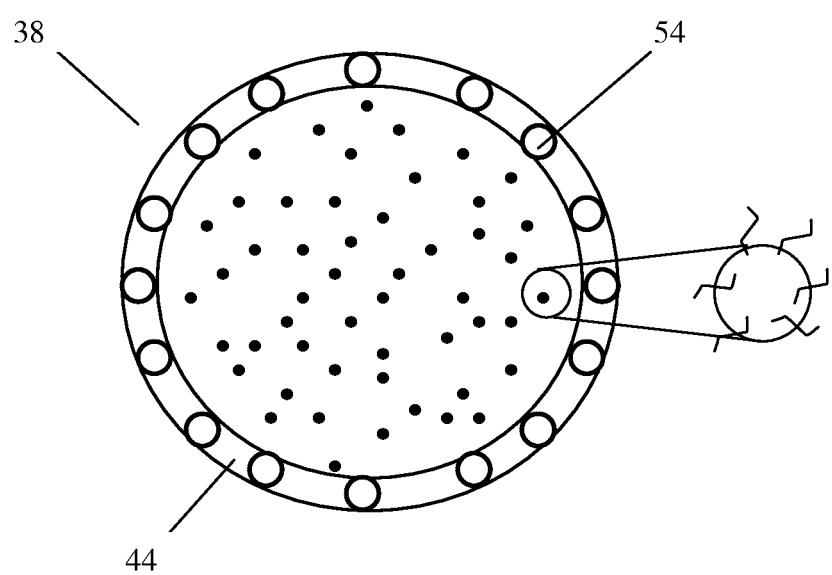
FIG. 13 is a side view of an encapsulated nucleotide tag complex with marker elements incorporated into the encapsulant layer.
Figure 14:
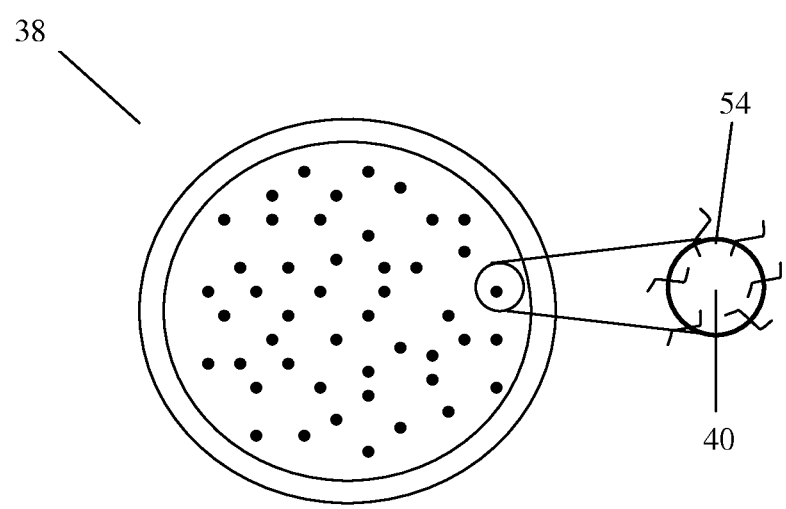
FIG. 14 is a side view of an encapsulated nucleotide tag complex with marker elements incorporated into the nanoparticles.
Figure 15:
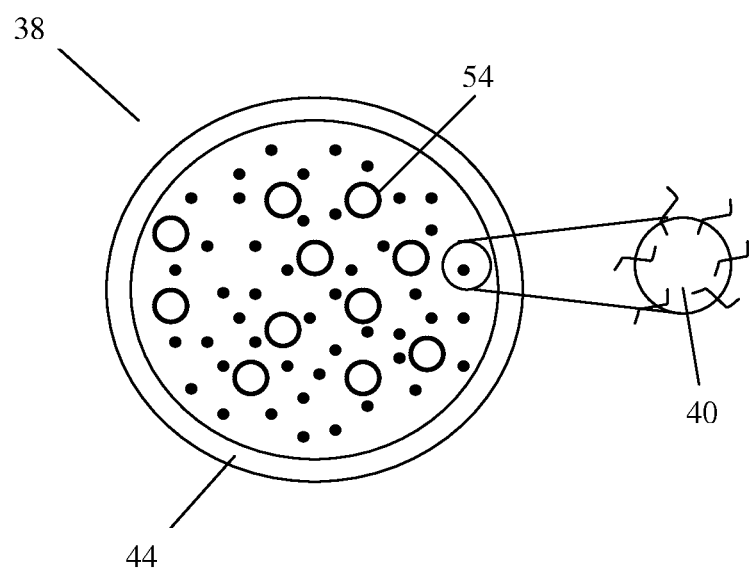
FIG. 15 is a side view of an encapsulated nucleotide tag complex with marker elements trapped inside the tag by the encapsulant layer.

The luminescent compound can be incorporated into the tag in a number of different ways. For example, in FIG. 11 the compound 54 is entirely separate from tag 38. In FIG. 12, compound 54 forms a layer on the exterior surface of encapsulant 44. The compound could also coat the interior surface of encapsulant 44. In FIG. 13, compound 54 is incorporated into encapsulant 44. In FIG. 14, compound 54 coats the surface of nucleotide-support platform 40. In FIG. 15, compound 54 is separate from nucleotide-support platform 40 and encapsulant 44 but is trapped within the interior of tag 38. In several of the described embodiments, the encapsulant layer must be designed to prevent inhibition of excitation and emission wavelengths.

If the seeded tags contain a photoluminescent compound, electromagnetic waves can be used to detect the presence of tags at a distance. Scanning equipment shines photons of the excitatory wavelength on the object of interest and looks for photons emitted at the proper wavelength as determined by the compound used in the tags. Detection of photons with the correct wavelength suggests that a nucleic acid-labeled tag is present and alerts the scanner that further investigation is necessary. The advantage of this system is that the scanning equipment and tag can be designed such that the individual doing the scanning does not have to be in close proximity to the object of interest.

The detection process can also be automated. An individual or object of interest can be forced to travel through a scanning point containing excitation equipment and emission detection equipment. As the individual or object of interest travels through the scanning point, the equipment scans for emitted photons of a certain wavelength. When the emitted photons are detected, a computer at the scanning point automatically alerts a remotely-located entity that subsequent analysis is necessary.

In yet another embodiment of the current invention, the nucleic acids contained within the tags taken from the surface of an object are analyzed using any method that determines the exact order of nucleotide bases. There are currently a number of different commonly-used sequencing techniques including but not limited to dye-terminator sequencing, parallel sequencing, and sequencing by ligation. Sequencing machines allow automated sequencing and can be run 24 hours a day. If PCR techniques are used, the appropriate primers are chosen based upon the types of tags known to be in the location of interest. Prior to sequencing or amplification, it is necessary to dissolve or otherwise remove the encapsulant layer from the tag in a manner that avoids inhibition of the downstream sequencing or PCR reactions. In the preferred embodiment, the encapsulant and/or agglomerate is disrupted by bead beater, a form of mechanical disruption. This one-step method avoids chemicals or extractions which could affect or inhibit PCR reactions.

In addition to the traditional sequencing techniques described above, real-time PCR and sequencing by hybridization techniques allow rapid detection of target nucleic acids. According to the real-time PCR technique, the extracted nucleic acid is placed into a well or tube that has been pre-loaded with all reagents necessary for a PCR reaction as well as a sequence-specific, nucleotide-based, fluorescently-labeled probe. As the extracted nucleic acid is amplified, the polymerase degrades the probe and releases the fluorescent reporter. The reporter immediately fluoresces and alerts the system to the presence of a tag nucleotide. Under the sequencing by hybridization technique, the extracted nucleic acid is labeled with a fluorescent marker and is hybridized to a DNA microarray that contains the complementary nucleotide sequence from known seeded tags. If the extracted nucleic acid hybridizes to any of the complementary tags, the fluorescent signal alerts the system to the presence of a target nucleic acid.

In step 26 of FIG. 2, the sequences obtained from the identified tags are compared to a database of sequences attached to seeded tags. To efficiently determine the point of origin or recent travel history of an object, the individuals analyzing tags detected in the field will need access or information about the tags dispersed by the seeder. A database of seeded tags will require maximum security measures to avoid improper access and manipulation, including access protection measures such as passwords. Standard computer algorithms are used to find exact or approximate matches between a sequence in the field and a tag sequence in the database. Once such a match is found, the user can reasonably suspect that the object of interest has recently traveled through the location seeded by that tag. If the real-time PCR or sequencing by hybridization techniques are used, the identification of the seeded tags is quickly determined by equipment that scans the plate or microarray for fluorescent label.

Step 28 of FIG. 2 is an optional step which is only required if the user is attempting to backtrack the route taken by an object of interest or extrapolate the object's point of origin. According to some uses of the present invention, simply learning that a person or object has traveled through a particular location is sufficient information. For other uses, it is necessary to analyze the sequences of multiple tags. To extrapolate a route taken or a point of origin, the seeded tag location information obtained by analyzing the surfaces of the object is fed into a computer algorithm that quickly plots every potential route that the object has traveled based upon the possible combinations of tag locations. A similar algorithm can be used to extrapolate a point of origin based upon the identified tag locations.

Although the present invention has been described in connection with a preferred embodiment, it should be understood that modifications, alterations, and additions can be made to the invention without departing from the scope of the invention as defined by the claims.

What is claimed is:

1. A method for determining whether an item has moved through a geographic location, the method comprising:
    seeding the geographic location with a nucleic acid tag comprising: an agglomerated plurality of nanoparticle nucleotide-support platforms each attached to a plurality of nucleic acid molecules, each of said nucleic acid molecules comprising identifying information, wherein a spacer is located between said nanoparticle nucleotide-support platform and said identifying information; an odorant; and an encapsulant surrounding said agglomerated plurality of nanoparticle nucleotide-support platforms and said plurality of nucleic acid molecules; and
    screening the item for the presence of the nucleic acid tag.

2. The method of claim 1, wherein each nucleic acid molecule comprises nucleotides selected from the group consisting of ribonucleotides, deoxyribonucleotides, and nucleotide analogues.

3. The method of claim 1, wherein said identifying information is encrypted within the nucleic acid molecules by altering the sequence of nucleotides.

4. The method of claim 1, wherein at least some of said nucleic acid tags comprise a retroreflector.

5. The method of claim 1, wherein the step of screening the item for the presence of the nucleic acid tag comprises the steps of:
    screening the item for the presence of said odorant; and
    if said odorant is present, characterizing said nucleic acid tag.

6. The method of claim 1, wherein the item is an incendiary device.

7. The method of claim 1, wherein the nucleic acid tag is characterized by sequencing all or part of the nucleic acid molecule.

8. The method of claim 1, wherein each geographic location is seeded with a unique nucleic acid tag.

* * * * *